(12) United States Patent
Doherty et al.

(10) Patent No.: US 6,369,034 B1
(45) Date of Patent: Apr. 9, 2002

(54) FUNCTIONALIZED ALKYL AND ALENYL SIDE CHAIN DERIVATIVES OF GLYCINAMIDES AS FARNESYL TRANSFERASE INHIBITORS

(75) Inventors: Annette Marian Doherty, Antony (FR); James Stanley Kaltenbronn, Ann Arbor, MI (US); Daniele Marie Leonard, Ann Arbor, MI (US); Dennis Joseph McNamara, Ann Arbor, MI (US); John Quin, III, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/646,147

(22) PCT Filed: Mar. 19, 1999

(86) PCT No.: PCT/US99/06090

§ 371 Date: Sep. 13, 2000

§ 102(e) Date: Sep. 13, 2000

(87) PCT Pub. No.: WO99/55725

PCT Pub. Date: Nov. 4, 1999

Related U.S. Application Data

(60) Provisional application No. 60/083,255, filed on Apr. 27, 1998.

(51) Int. Cl.[7] .................... A61K 38/05; C07D 233/56; C07K 5/06
(52) U.S. Cl. .................. 514/19; 548/338.1; 546/210; 544/139; 514/400; 514/326; 514/235.8
(58) Field of Search .................. 514/400, 235.8, 514/326, 19, 18; 548/338.1; 544/139; 546/210

(56) References Cited

FOREIGN PATENT DOCUMENTS

| WO | 95 09001 | 4/1995 |
|----|----------|--------|
| WO | 95 12612 | 5/1995 |
| WO | 96 00736 | 1/1996 |
| WO | 97 44350 | 11/1997 |
| WO | 98 27109 | 6/1998 |
| WO | 98 46625 | 10/1998 |

OTHER PUBLICATIONS

McNamara, D. et al., J of Medicinal Chemistry, C–Terminal Modifications of Histidyl–N–Benzylglycinamides to Give Improved Inhibition of RAS Farnesyltransferase, Cellular Activity, and Anticance Activity in Mice, 1997, vol. 40:21 pp 3319–3322.

*Primary Examiner*—Charandit S. Awlakh
(74) *Attorney, Agent, or Firm*—Charles W. Ashbrook

(57) ABSTRACT

The present invention provides compounds of Formula (I). The present invention also provides a method of treating cancer and treating or preventing restenosis or atherosclerosis. Also provided by the present invention is a pharmaceutically acceptable composition containing a compound of Formula (I).

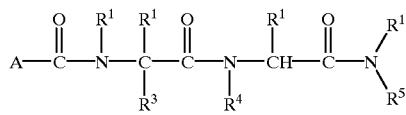

16 Claims, No Drawings

FUNCTIONALIZED ALKYL AND ALENYL SIDE CHAIN DERIVATIVES OF GLYCINAMIDES AS FARNESYL TRANSFERASE INHIBITORS

This application is a 371 of PCT/US99/06090 filed Mar. 19, 1999. Which claims benefit of Provisional Ser. No. 60/083,255 filed Apr. 27, 1998.

FIELD OF THE INVENTION

The present invention relates to compounds that can be used to treat, prophylactically or otherwise, uncontrolled or abnormal proliferation of tissues. Specifically, the present invention relates to compounds that inhibit the farnesyl transferase enzyme, which has been determined to activate ras proteins that in turn activate cellular division and are implicated in cancer, restenosis, and atherosclerosis.

BACKGROUND OF THE INVENTION

Ras protein (or p21) has been examined extensively because mutant forms are found in 20% of most types of human cancer and greater than 50% of colon and pancreatic carcinomas (Gibbs J. B., *Cell,* 1991;65:1, Cartwright T. et al., *Chimica. Oggi.,* 1992; 10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J. et al., *Microbiol. Rev.,* 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis and atherosclerosis are such conditions. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J. et al., *Hypertension,* 1989; 13:706 and *J. Clin. Invest.,* 83:1419; Gibbons G. H. et al., *Hypertension,* 1989;14:358; Satoh T. et al., *Molec. Cell. Biol.,* 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis or atherosclerosis, particularly in those instances where normal ras expression and/or function is exaggerated by growth stimulatory factors. See, for example, Kohl et al., *Nature Med.,* 1995;1(8):792–748.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesyl pyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F. et al., *Cell,* 1989;57:1617; Schafer W. R. et al., *Science,* 1989;245:379; Casey P. J., *Proc. Natl. Acad. Sci. USA,* 1989;86:8323).

Recently, protein farnesyl transferases (PFTs), also referred to as farnesyl proteintransferases (FPTs), have been identified and a specific PFT from rat brain was purified to homogeneity (Reiss Y. et al., *Bioch. Soc. Trans.,* 1992;20:487–88). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W.-J. et al., *J. Biol. Chem.,* 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme responsible for the post-translational modification of the ras protein which helps to anchor the protein product of the ras gene to the cell membrane. The role of the ras mutation in transducing growth signals within cancer cells relies on the protein being in the cell membrane so with farnesyl transferase inhibited, the ras protein will stay in the cytosol and be unable to transmit growth signals: these facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma and human colon carcinoma xenografts in nude mice (Nagasu T. et al., *Cancer Res.,* 1995;55:5310–5314). Furthermore, inhibition of tumor growth by B956 has been shown to correlate with inhibition of ras posttranslational processing in the tumor. Other ras farnesyl transferase inhibitors have been shown to specifically prevent ras processing and membrane localization and are effective in reversing the transformed phenotype of mutant ras containing cells (Sepp-Lorenzino L. et al., *Cancer Res.,* 1995;55:5302–5309).

In another report (Sun J. et al., *Cancer Res.,* 1995;55:4243–4247), a ras farnesyl transferase inhibitor FT1276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8):792–748). Thus, ras farnesyl transferase inhibitors have benefit in certain forms of cancer, particularly those dependent on oncogenic ras for their growth. However, it is well-known that human cancer is often manifested when several mutations in important genes occurs, one or more of which may be responsible for controlling growth and metastases. A single mutation may not be enough to sustain growth and only after two of three mutations occur, tumors can develop and grow. It is therefore difficult to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni et al., *Oncogene*, 1995;10:1905–1913). Therefore, ras farnesyl transferase inhibitors could also block the prenylation of the above proteins and therefore would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C. et al., *Nature Med.*, 1995;1(6):541–545). This report definitively supports a role for farnesyl transferase inhibitors in this disease, showing inhibition of accumulation and proliferation of vascular smooth muscle.

SUMMARY OF THE INVENTION

The present invention provides compounds having the Formula I

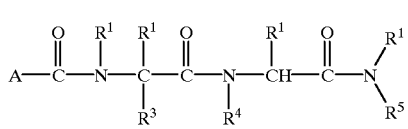

wherein

A is

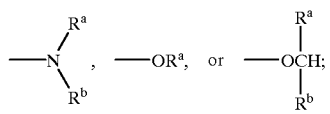

each $R^1$ and $R^b$ are independently hydrogen or $C_1$–$C_6$ alkyl;
each $R^a$ is independently $C_1$–$C_6$ alkyl, —$(CH_2)_m$-aryl, —$(CH_2)_m$-substituted aryl, —$(CH_2)_m$-substituted heteroaryl, or —$(CH_2)_m$-heteroaryl;
each m is independently 0 to 3;
each n is independently 1 to 4;

$R^3$ is

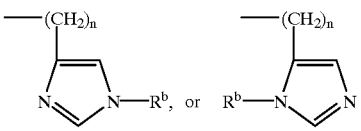

$R^4$ is

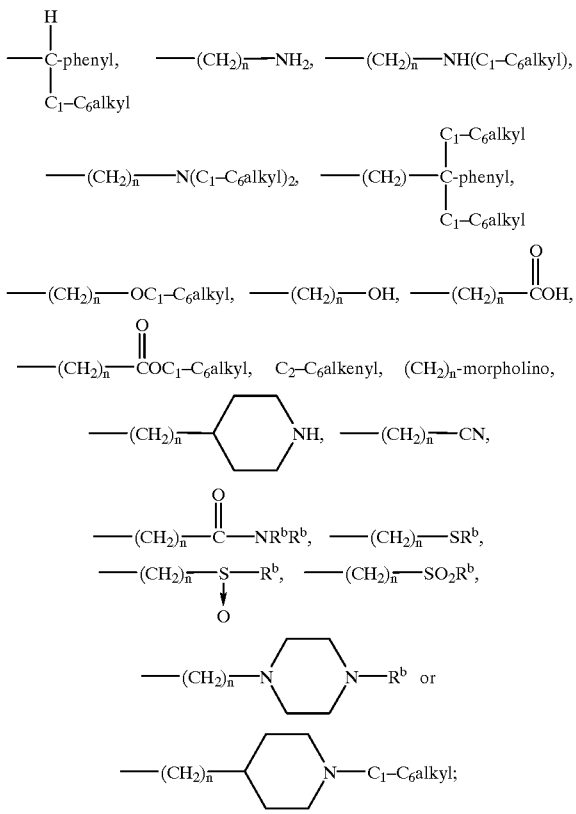

$R^5$ is

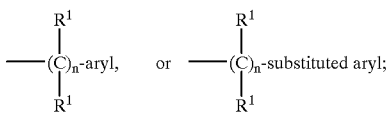

and the pharmaceutically acceptable salts, esters, amides, and prodrugs thereof.

In a preferred embodiment of the compounds of Formula I, each $R^1$ is hydrogen.

In another preferred embodiment of the compounds of Formula I, A is —$OCH_2$-phenyl.

In another preferred embodiment of the compounds of Formula I, $R^5$ is

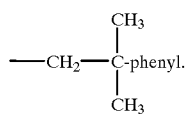

In another preferred embodiment of the compound of Formula I,

A is —OCH$_2$-phenyl;

each $R^1$ is hydrogen; and $R^5$ is

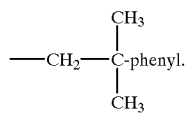

Also provided are compounds having the Formula I

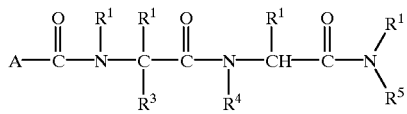

wherein

A is —OCH$_2$-phenyl, or

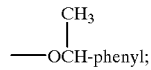

each $R^1$ is hydrogen;

$R^3$ is

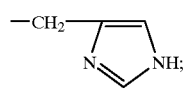

$R^4$ is

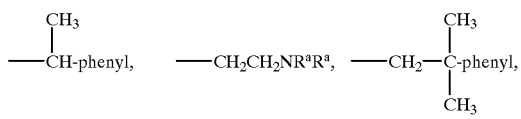

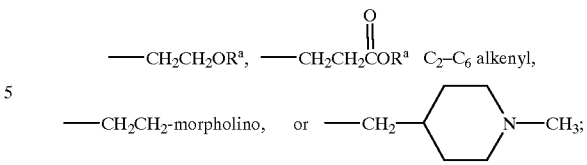

each $R^a$ is independently hydrogen or $C_1$–$C_6$ alkyl;

$R^5$ is

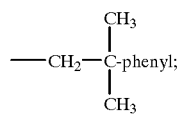

and the pharmaceutically acceptable salts, esters, amides, and prodrugs thereof.

The present invention also provides a pharmaceutical composition comprising a compound of Formula I.

Also provided is a method of treating cancer, the method comprising administering to a patient having cancer a therapeutically effective amount of a compound of Formula I.

Also provided is a method of treating atherosclerosis, the method comprising administering to a patient having atherosclerosis a therapeutically effective amount of a compound of Formula I.

Also provided is a method of treating or preventing restenosis, the method comprising administering to a patient having restenosis or at risk of developing restenosis, a therapeutically effective amount of a compound of Formula I.

The present invention provides the compounds:

Benzyl N-((1S)-1-(1H-4-imidazolylmethyl)-2-2-[(2-methyl-2-phenylpropyl)amino]-2-oxoethyl [(1S)-1-phenylethyl]amino-2-oxoethyl)carbamate;

Benzyl N-((1S)-1-(1H-4-imidazolylmethyl)-2-2-[(2-methyl-2-phenylpropyl)amino]-2-oxoethyl[(1R)-1-phenylethyl]amino-2-oxoethyl)carbamate;

Benzyl N-[(1S)-1-(1H-4-imidazolylmethyl)-2-((2-methyl-2-phenylpropyl)2-[(2-methyl-2-phenylpropyl)amino]-2-oxoethylamino)-2-oxoethyl]carbamate;

Methyl 3-([[(2S)-2-[(benzyloxy)carbonyl]amino-3-(1H-4-imidazolyl)propanoyl]-2-[(2-methyl-2-phenylpropyl)amino]-2-oxoethylamino)propanoate;

3-([[(2S)-2-[(Benzyloxy)carbonyl]amino-3-(1H-4-imidazolyl)propanoyl]-2-[(2-methyl-2-phenylpropyl)amino]-2-oxoethylamino)propanoic acid;

[1-{(2-Amino-ethyl)-[(2-methyl-2-phenyl-propylcarbamoyl)-methyl]-carbamoyl}-2-(3H-imidazol-4-yl)-ethyl]-carbamic acid benzyl ester;

Benzyl N-[(1S)-1-(1H-4-imidazolylmethyl)-2-([2-(methylamino)ethyl]-2-[(2-methyl-2-phenylpropyl)amino]-2-oxoethylamino)-2-oxoethyl]carbamate;

(2-(3 H-Imidazol-4-yl)-1-{(2-methoxy-ethyl)-[(2-methyl-2-phenyl-propylcarbamoyl)-methyl]-carbamoyl}-ethyl)-carbamic acid benzyl ester;

Benzyl N-[2-((E)-2-butenyl-2-[(2-methyl-2-phenylpropyl)amino]-2-oxoethylamino)-1-(1H-4-imidazolylmethyl)-2-oxoethyl]carbamate;

$R^3$ is

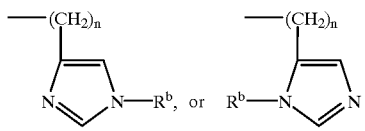

$R^4$ is

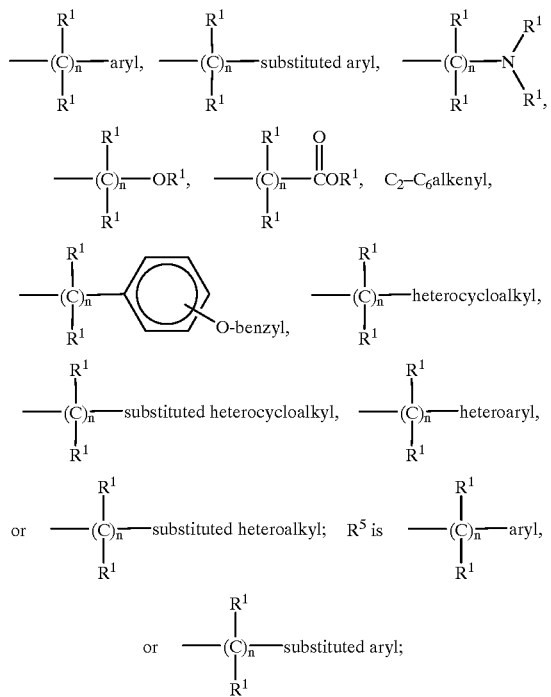

and the pharmaceutically acceptable salts, esters, amides, and prodrugs thereof.

[1-{(4-Benzyloxy-benzyl)-[(2-methyl-2-phenyl-propylcarbamoyl)-methyl]-carbamoyl}2-(1H-imidazol-4-yl)-ethyl]-carbamic acid 1-phenyl-ethyl ester;

Benzyl N-(1S)-1-(1H-4-imidazolylmethyl)-2-[2-[(2-methyl-2-phenylpropyl)amino]-2-oxoethyl(2-morpholinoethyl)amino]-2-oxoethylcarbamate;

3-{[2-Benzyloxycarbonylamino-3-(3H-imidazol-4-yl)-propionyl]-[(2-methyl-2-phenyl-propylcarbamoyl)-methyl]-amino}-propionic acid isopropyl ester;

[1-{(2-Dimethylcarbarnoyl-ethyl)-[(2-methyl-2-phenyl-propylcarbamoyl)-methyl]-carbamoyl}-2-(3H-imidazol-4-yl)ethyl]-carbamic acid benzyl ester;

{2-(3H-Imidazol-4-yl)-1-[[(2-methyl-2-phenyl-propylcarbamoyl)-methyl]-(2-methylsulfanyl-ethyl)-carbamoyl]-ethyl}-carbamic acid benzyl ester;

Benzyl N-[(1S)-2-((2-hydroxyethyl)2-[(2-methyl-2-phenylpropyl)amino]-2-oxoethylamino)-1-(1H-4-imidazolylmethyl)-2-oxoethyl]carbamate; and Benzyl N-((1S)-1-(1H-4-imidazolylmethyl)-2-2-[(2-methyl-2-phenylpropyl)amino]-2-oxoethyl[(1-methyl4-piperidyl)methyl]amino-2-oxoethyl)carbamate.

The present invention also provides compounds having the Formula I

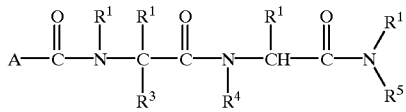

wherein

A is

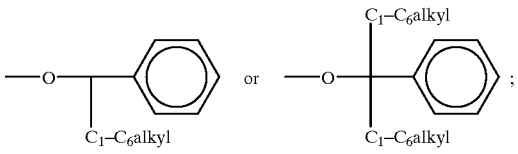

each $R^1$ and $R^b$ are independently hydrogen or $C_1$–$C_6$ alkyl;

each n is independently 1 to 4;

DETAILED DESCRIPTION OF THE INVENTION

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, —CN, Cl, Br, I, $CF_3$, $NO_2$, $NH_2$, $NHCH_3$, $N(CH_3)_2$, NHCO-alkyl, $(CH_2)_mCO_2H$, $(CH_2)_mCO_2$-alkyl, $(CH_2)_mSO_3H$, —NH alkyl, —N(alkyl)$_2$, —$(CH_2)_mPO_3H_2$, $(CH_2)_mPO_3(alkyl)_2$, $(CH_2)_mSO_2NH_2$, and $(CH_2)_mSO_2NH$-alkyl wherein alkyl is defined as above and m is 0, 1, 2, or 3.

The term "heteroaryl" means an aromatic ring containing one or more heteroatoms. Examples of heteroaryl radicals include thienyl, furanyl, pyrrolyl, pyridyl, imidazoyl, or indolyl group, substituted or unsubstituted by 1 or 2 substituents from the group of substituents described above for aryl. Examples of heteroatoms include nitrogen, oxygen, sulfur, and phosphorus.

The term "halogen" includes chlorine, fluorine, bromine, and iodine.

The term "alkenyl" means a branched or straight chain hydrocarbon having one or more carbon-carbon double bond.

The term "heterocycle" or "heterocycloalkyl" means a cycloalkyl group wherein one or more carbon atom is replaced with a heteroatom. Examples of heterocycles include, but are not limited to, pyrrolidinyl, piperidinyl, and piperazinyl.

The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of restenosis, cancer, or atherosclerosis or prevents restenosis. A therapeutically effective amount of a compound of the present invention can be easily determined by one skilled in the art by administering a quantity of a compound to a patient and observing the result. In addition, those skilled in the art are familiar with identifying patients having cancer, restenosis, or atherosclerosis or who are at risk of having restenosis.

The term "cancer" includes, but is not limited to, the following cancers:

breast;

ovary;

cervix;

prostate;

testis;

esophagus;

glioblastoma;

neuroblastoma;

stomach;

skin, keratoacanthoma;

lung, epidermoid carcinoma, large cell carcinoma, adenocarcinoma;

bone;

colon, adenocarcinoma, adenoma;

pancreas, adenocarcinoma;

thyroid, follicular carcinoma, undifferentiated carcinoma, papillary carcinoma;

seminoma;

melanoma;

sarcoma;

bladder carcinoma;

liver carcinoma and biliary passages;

kidney carcinoma;

myeloid disorders;

lymphoid disorders, Hodgkins, hairy cells;

buccal cavity and pharynx (oral), lip, tongue, mouth, pharynx;

small intestine;

colon-rectum, large intestine, rectum;

brain and central nervous system; and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylarnine, triethylamine, ethylamine, and the like. (See, for example, Berge S. M. et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), Cremophor E. L., (a derivative of castor oil and ethylene oxide; purchased from Sigma Chemical Co., St. Louis, Mo.), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor E. L., (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

PFT Inhibitory Activity

The protein:farnesyl transferase (PFT) or farnesyl protein transferase (FPT) inhibitory activity of compounds of the present invention were assayed in HEPES buffer (pH 7.4) containing 5 mM potassium phosphate and 20 $\mu$M $ZnCl_2$. The solution also contained 5 mM DTT (dithiothreitol), 5 mM $MgCl_2$, and 0.1% PEG 8000. Assays were performed in 96 well plates (Wallec) and employed solutions composed of varying concentrations of a compound of the present invention in 10% DMSO (dimethylsulfoxide). Upon addition of both substrates, radiolabeled farnesyl pyrophosphate ([$1^3$H], specific activity 15–30 Ci/mmol, final concentration 134 nM) and (biotinyl)-Ahe-Thr-Lys-Cys-Val-Ile-Met ([3aS[3a alpha, 4 beta, 6a alpha]-hexahydro-2-oxo-1H-thieno[3,4-d] imidazole-5-pentanoic acid]-[7-aminoheptanoic acid]-Thr-Lys-Cys-Val-Ile-Met) (Ahe is 7-aminoheptanoic acid, Thr is threonine, Lys is lysine, Cys is cysteine, Val is valine, Ile is isoleucine, and Met is methionine) (final concentration 0.2 4$\mu$M), the enzyme reaction was started by addition of SF9 affinity purified rat FPT. After incubation at 30° C. for 30 minutes, the reaction was terminated by diluting the reaction 2.5-fold with a stop buffer containing 1.5 M magnesium acetate, 0.2 M $H_3PO_4$, 0.5% BSA (bovine serum albumin), and strepavidin beads (Amersham) at a concentration of 1.3 mg/mL. After allowing the plate to settle for 30 minutes at room temperature, radioactivity was quantitated on a micro-Beta counter (Model 1450, Wallec). The assay was also carried out without 5 mM potassium phosphate.

Gel Shift Assay

Twenty-four hours after planting $2 \times 10^6$ ras-transformned cells per treatment condition, the farnesylation inhibitor is added at varying concentrations. Following an 18-hour incubation period, cells are lysed in phosphate-buffered saline containing 1% Triton X-100, 0.5% sodium deoxycholate, and 0.1% SDS (sodium dodecyl sulfate), pH 7.4 in the presence of several protease inhibitors (PMSF (phenylmethylsulfonylfluoride), antipain, leupeptin, pepstatin A, and aprotinin all at 1 µg/mL). Ras protein is immunoprecipitated from the supernatants by the addition of 3 µg v-H-ras Ab-2 (Y13-259 antibody from Oncogene Science). After overnight immunoprecipitation, 30 µL of a 50% protein G-Sepharose slurry (Pharmacia) is added followed by 45-minute incubation. Pellets are resuspended in 2×tris-glycine loading buffer (Novex) containing 5% mercaptoethanol and then denatured by 5 minutes boiling prior to electrophoresis on 14% Tris-glycine SDS gels. Using Western transfer techniques, proteins are transferred to nitrocellulose membranes followed by blocking in blocking buffer. Upon overnight incubation with primary antibody (pan-ras Ab-2 from Oncogene Science), an antimouse HRP (horse radish peroxidase) conjugate secondary antibody (Amersham) is employed for detection of the ras protein.

Blots are developed using ECL(enhanced chemiluminescence) techniques (Amersham).

The compounds of the present invention can be synthesized as follows.

Scheme 1 shows a method by which the compounds of the present invention can be prepared, by illustrating the synthesis of Example 1, benzyl N-((1S)-1-(1H-4-imidazolylmethyl)-2-2-[(2-methyl-2-phenylpropyl)amino]-2-oxoethyl[(1S)-1-phenylethyl]amino-2-oxoethyl) carbamate. Reaction of (S)-α-methylbenzylamine with methyl bromoacetate was carried out in acetonitrile in the presence of diIsopropylethylamine as the base to give methyl-2-[(1S)-1-phenylethyl]aminoacetate. Methyl-2-[(1S)-1-phenylethyl]aminoacetate was then coupled to Cbz-His(trityl) in methylene chloride with HATU as coupling agent, and diisopropylethylamine as the base. The resulting product was saponified using lithium hydroxide at 0° C., followed by coupling with β,β-dimethylphenethylamine in methylene chloride, with HBTU as coupling agent, and diisopropylethylamine as the base. The trityl group was removed by treatment with 50% TFA in methylene chloride. The β,β-dimethylphenethylamine was prepared from benzyl cyanide, which was treated with 2 equivalents of sodium hydride in tetrahydrofuran (THF) and 2 equivalents of methyl iodide in THF followed by hydrogenation ($H_2$, Pd/C, ammonia) and treatment with HCl to give the HCl salt.

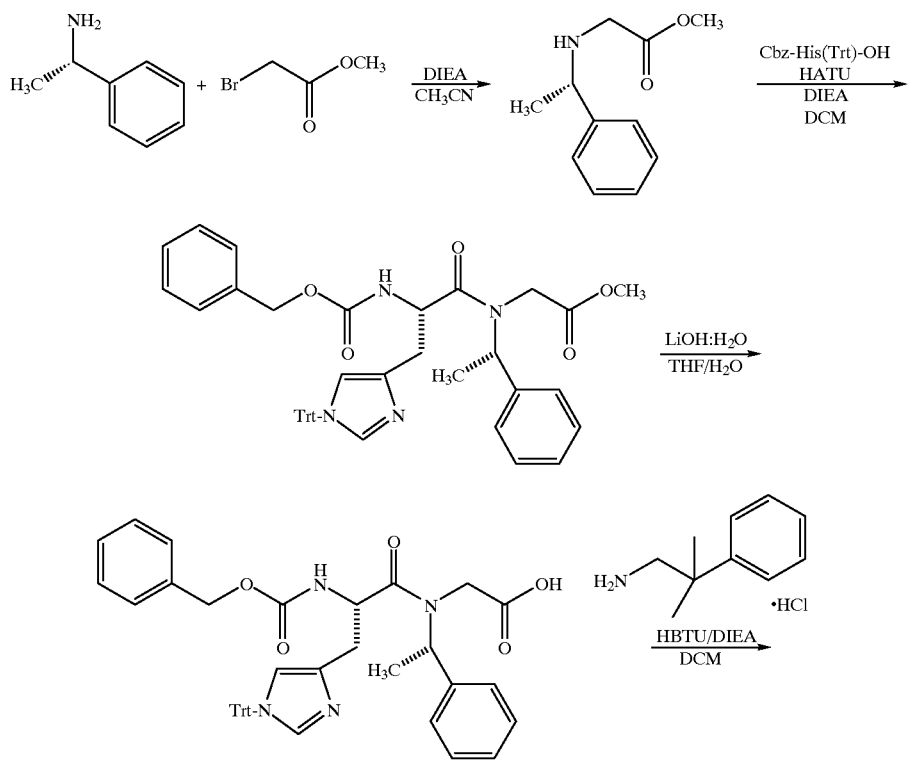

Scheme 1

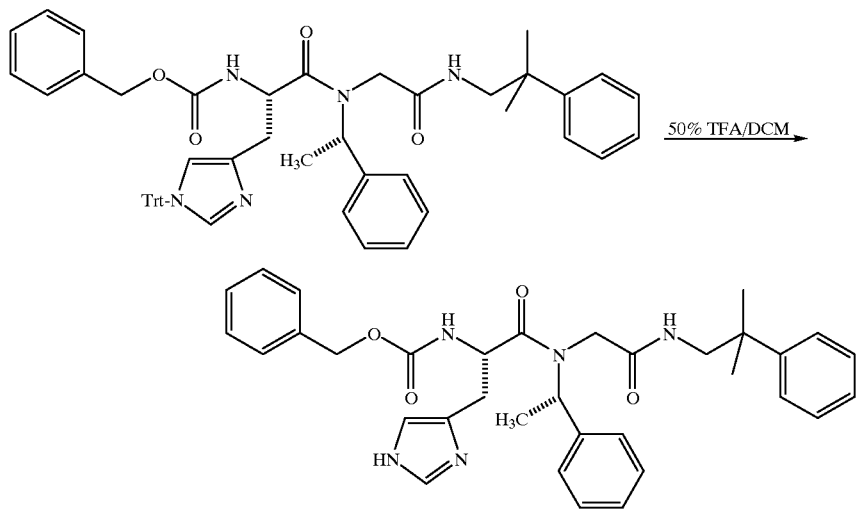

Scheme 2 shows a method by which the compounds of the present invention can be prepared, by illustrating the synthesis of Example 4, methyl 3-([(2S)-2-[(benzyloxy)carbonyl]amino-3-(1H-4-imidazolyl)propanoyl]-2-[(2-methyl-2-phenylpropyl)amino]-2-oxoethylamino)propanoate. Reaction of β-alanine methyl ester hydrochloride with t-butyl bromoacetate was carried out in methylene chloride in the presence of triethylamine as the base to give 3-(tert-butoxycarbonylmethyl-amino)-propionic acid methyl ester which was then coupled to Cbz-His(trityl) in methylene chloride/acetonitrile with HBTU as coupling agent, and triethylamine as the base. The resulting product was treated with 95% aqueous TFA, to remove the trityl and the t-butyl groups, followed by coupling with β,β-dimethylphenethylamine in methylene chloride/dimethylformamide, with HBTU as coupling agent, and diisopropylethylamine as the base to give the desired product.

Scheme 2

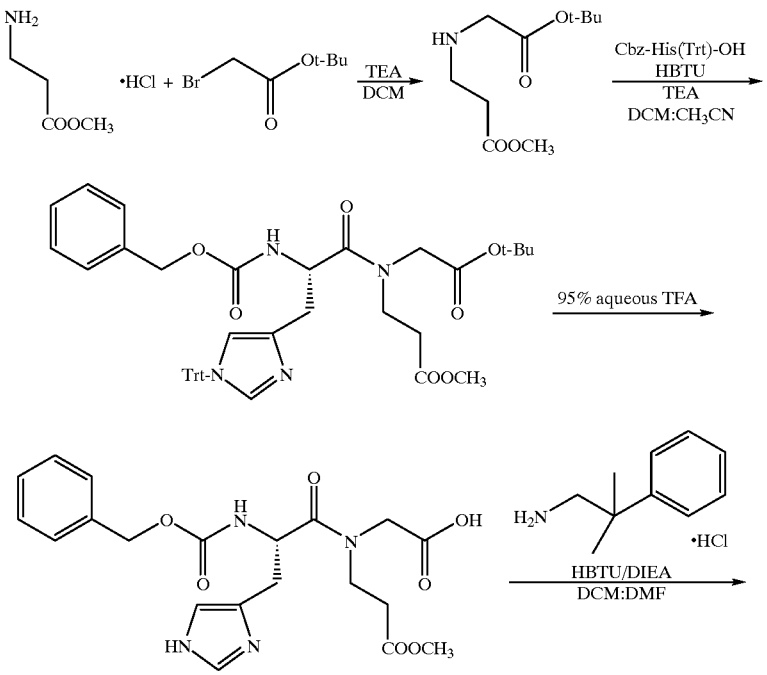

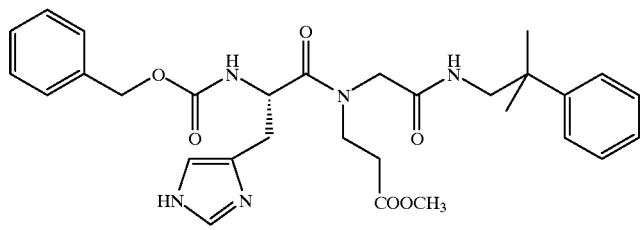

Scheme 3 shows a method by which the compounds of the present invention can be prepared, by illustrating the synthesis of Example 6, [1-{(2-Amino-ethyl)-[(2-methyl-2-phenyl-propylcarbamoyl)-methyl]-carbamoyl}-2-(3H-imidazol-4-yl)-ethyl]-carbamic acid benzyl ester. Reaction of (2-aminoethyl) carbamic acid tert-butyl ester with methyl bromoacetate was carried out in methylene chloride in the presence of triethylamine as the base to give (2-tert-butoxycarbonylamino-ethylamino)-acetic acid methyl ester hydrochloride which was then coupled to Cbz-His(trityl) in methylene chloride/dimethylformamide with HATU and HOAt as coupling agents, and diisopropylethylamine as the base. The resulting product was saponified using sodium hydroxide, followed by coupling with β,β-dimethylphenethylamine in methylene chloride, with PyBOP as coupling agent, and diisopropylethylamine as the base. The trityl and Boc groups were removed by treatment with 95% aqueous TFA.

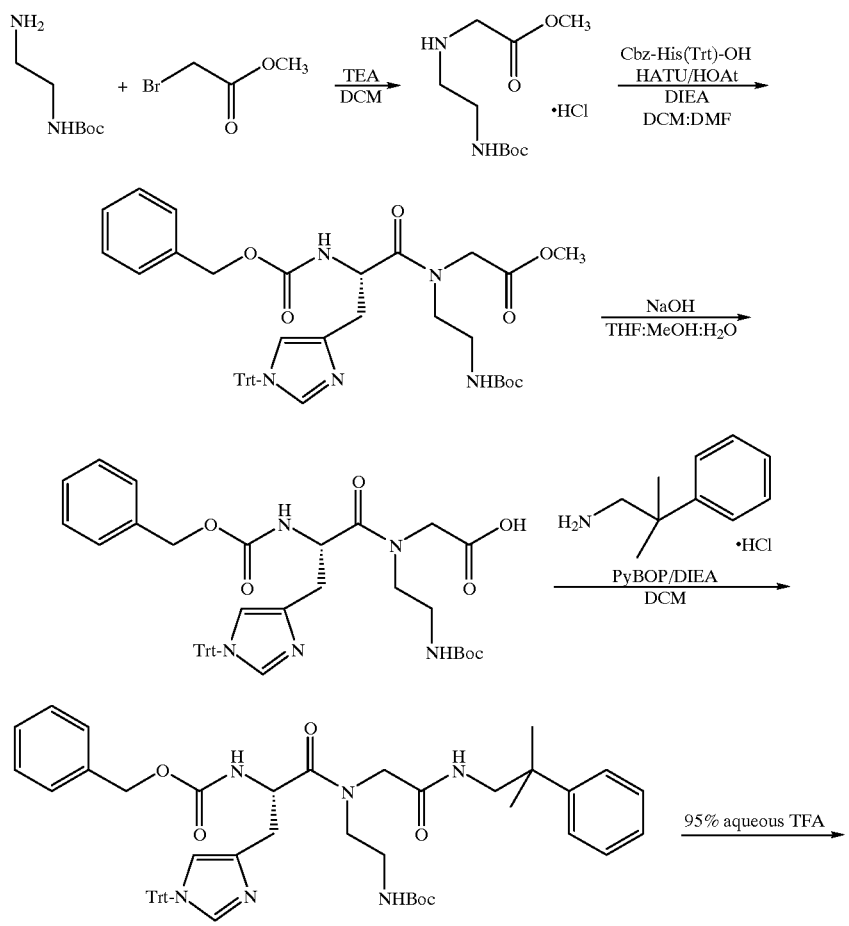

Scheme 3

-continued

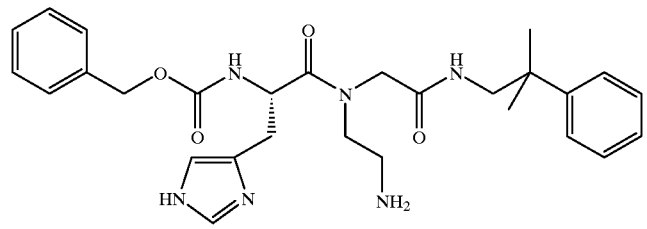

Scheme 4 shows a method by which the compounds of the present invention can be prepared, by illustrating the synthesis of Example 9, benzyl N-[2-((E)-2-butenyl-2-[(2-methyl-2-phenylpropyl)amino]-2-oxoethylamino)-1-(1H-4-imidazolylmethyl)-2-oxoethyl]carbamate. Reaction of (E)-2-buten-1-amine hydrochloride with methyl bromoacetate was carried out in acetonitrile in the presence of triethylamine as the base to give methyl 2-[(E)-2-butenylamino]-acetate which was then coupled to Cbz-His(trityl) in methylene chloride with PyBOP as coupling agent, and diisopropylethylamine as the base. The resulting product was saponified using sodium hydroxide, followed by coupling with β,β-dimethylphenethylamine in tetrahydrofuran, with DCC and HOBt as coupling agents, and triethylamine as the base. The trityl group was removed by treatment with 80% aqueous acetic acid.

Scheme 4

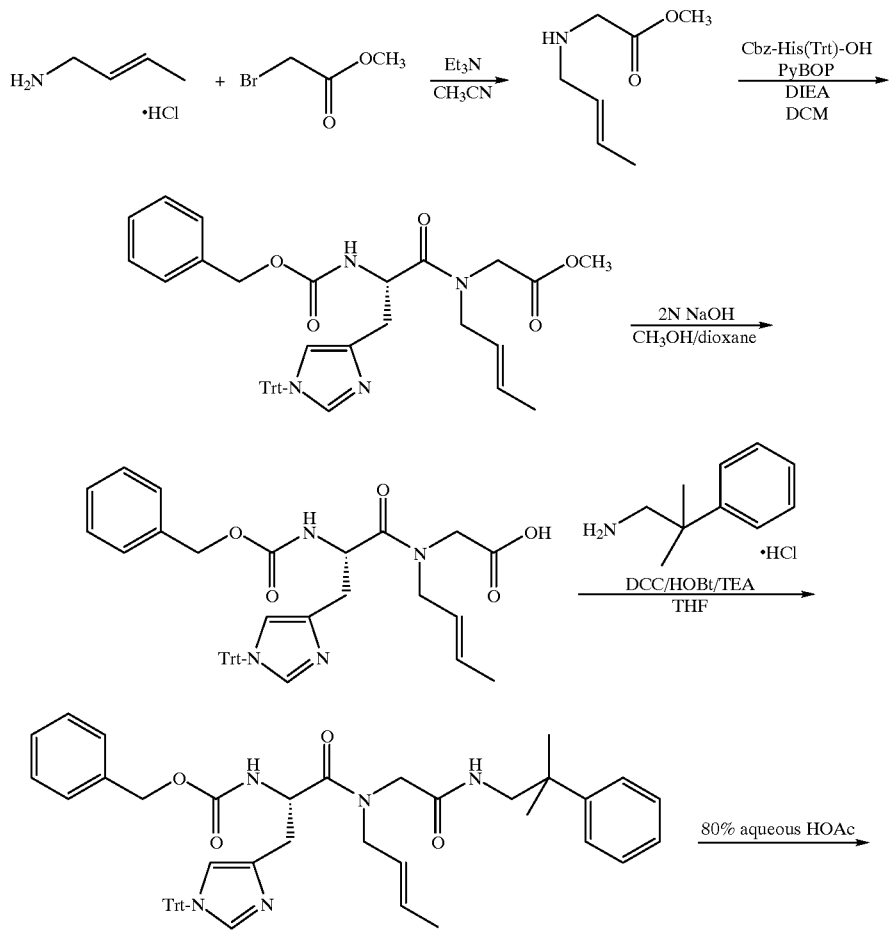

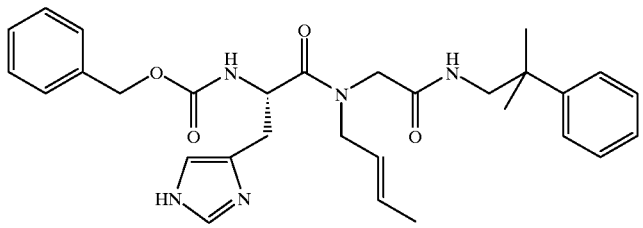

EXAMPLE 1

Benzyl N-((1S)-1-(1H-4-imidazolylmethyl)-2-2-[(2-methyl-2-phenylpropyl)amino]-2-oxoethyl[(1S)-1-phenylethyl]amino-2-oxoethyl)carbamate

Step 1: Methyl 2-[(1S)-1-phenylethyl]aminoacetate

To a solution of (S)-α-methylbenzylamine (3.87 mL, 0.03 mol) in acetonitrile (50 mL) was added diisopropylethylamine (5.23 mL, 0.03 mol), followed by methyl bromoacetate (2.84 mL, 0.03 mol). The reaction was stirred under nitrogen, at room temperature, overnight. The solution was concentrated and the residue partitioned between ethyl acetate and saturated $NaHCO_3$. The aqueous layer was separated, and the product extracted three times with ethyl acetate. The ethyl acetate solutions were combined, washed three times with brine, dried over $MgSO_4$, and concentrated to give a light yellow liquid. Chromatography was carried out on silica gel, using ethyl acetate as eluent, to give a colorless liquid; 4.97 g (86% yield). MS-APCI: M+1=194.2.

Step 2: Methyl 2-[(2S)-2-[(benzyloxy)carbonyl]amino-3-(1-trityl-1H-4-imidazolyl)propanoyl][(1S)-1-phenylethyl]aminoacetate The compound from Step 1 (0.54 g, 2.8 mmol), Cbz-His(Trt)-OH (Hudspeth, J. P., Kaltenbronn, J. S., Repine, J. T., Roark, W. H., Stier, M. A. Renin Inhibitors III, U.S. Pat. No. 4,735,933; 1988) (1.49 g, 2.8 mmol) and HATU (1.28 g, 3.4 mmol) were mixed in methylene chloride (10 mL), at 0° C. Diisopropylethylamine (0.97 mL, 5.6 mmol) was then added. The reaction was left to warm to room temperature and was stirred overnight under nitrogen. The solution was concentrated and the residue taken up in ethyl acetate. The ethyl acetate was washed twice with 0.1N HCl, saturated $NaHCO_3$, and brine, dried over $MgSO_4$, filtered and concentrated to give a slightly yellow foam. Chromatography was carried out on silica gel, using $10:1/CH_2Cl_2:CH_3OH$ as eluent, to give a white foam; 0.89 g (45% yield). MS-APCI: M+1=707.4

Step 3: 2-[(2S)-2-[(Benzyloxy)carbonyl]amino-3-(1-trityl-1H-4-imidazolyl)propanoyl][(1S)-1-phenylethyl]aminoacetic acid To a solution of compound from Step 2 (0.88 g, 1.24 mmol) in tetrahydrofuran (12 mL), was added water (4 mL), followed by $LiOH:H_2O$ (0.104 g, 2.49 mmol). The suspension was stirred at room temperature, overnight. The solution was concentrated, the residue diluted with water and 1 N HCl (3 mL) was then added. The product was extracted four times with ethyl acetate. The ethyl acetate solution was washed with brine, dried over $MgSO_4$, filtered, concentrated to give a white foam. Chromatography was carried out on silica gel, using $10:1/CH_2Cl_2:CH_3OH$ as eluent, to give a white foam; 0.61 g (71% yield). MS-APCI: M+1=693.5

Step 4: Benzyl N-(1S)-2-2-[(2-methyl-2-phenylpropyl)amino]-2-oxoethyl[(1S)-1-phenylethyl]amino-2-oxo-1-[(1-trityl-1H-4-imidazolyl)methyl]ethylcarbamate A suspension of compound from Step 3 (0.61 g, 0.88 mmol), β,β-dimethylphenethylamine hydrochloride (from Step 6, below) (0.190 g, 1 mmol), and HBTU (0.379 g, 1 mmol) in methylene chloride (10 mL) was stirred and cooled to 0° C., and treated with diisopropylethylamine (0.47 mL, 2.7 mmol) dropwise. The reaction was warmed to room temperature and stirred overnight. The solution was concentrated and the residue was taken up in ethyl acetate. The ethyl acetate was washed with 1N HCl saturated $NaHCO_3$ and brine, dried over $MgSO_4$, filtered and concentrated to give a light tan foam. Chromatography was carried out on silica gel, using $10:1/CH_2Cl_2:CH_3OH$ as eluent, to give a white foam; 0.53 g (73% yield). MS-APCI: M+1=824.6.

Step 5: Benzyl N-((1S)-1-(1H-4-imidazolylmethyl)-2-2-[(2-methyl-2-phenylpropyl)amino]-2-oxoethyl[(1S)-1-phenylethyl]amino-2-oxoethyl)carbamate The compound from Step 4 (0.53 g, 0.64 mmol) was treated with methylene chloride (10 mL) and trifluoroacetic acid (10 mL) for 2 hours at room temperature. The solution was concentrated and the residue taken up in ethyl acetate. The ethyl acetate solution was washed with saturated $NaHCO_3$, dried over $MgSO_4$, filtered and concentrated to give a white foam. Chromatography was carried out on silica gel, using $10:1/CH_2Cl_2:CH_3OH$ as eluent, to give a white foam; 0.28 g (74% yield). MS-APCI: M+1=582.4.

Analysis calculated for $C_{34}H_{39}N_5O_4.0.3H_2O$: C, 69.56; H, 6.80; N, 11.93.

Found: C, 69.39; H, 6.82; N, 11.91.

Step 6: β,β-Dimethylphenethylamine hydrochloride

Sodium hydride (60% in mineral oil) (17 g, 0.43 mol) was suspended in tetrahydrofuran (150 mL) and cooled to 0° C. under nitrogen. Benzyl cyanide (22.2 g, 0.19 mol) in tetrahydrofuran (30 mL) was added dropwise, and the reaction was left to stir for 1 hour. Iodomethane (24.9 mL, 0.4 mol) in tetrahydrofuran (20 mL) was added dropwise at 0° C. The reaction was stirred at room temperature overnight, under nitrogen. The solution was filtered and the filtrate was concentrated. The residue was taken up in ethyl acetate (100 mL) and washed three times with 10% $NaHSO_3$, saturated $NaHCO_3$, brine and dried over $MgSO_4$, filtered and concentrated; 22.74 g (92% yield).

The above product was reduced in the presence of Raney nickel, in methanol/$NH_3$. The catalyst was removed and washed with methanol. The filtrate was concentrated and diethyl ether (100 mL) was added to the residue. Concentrated HCl was added dropwise to precipitate the desired product; 24,8 g (86% yield).

EXAMPLE 2

Benzyl N-((1S)-1-(1H-4-imidazolylmethyl)-2-2-[(2-methyl-2-phenylpropyl)amino]-2-oxoethyl[(1R)-1-phenylethyl]amino-2-oxoethyl)carbamate The title compound can be prepared according to Example 1 by substituting (R)-α-methylbenzylamine for (S)-α-methylbenzylamine in Step 1. The title compound is obtained as a white foam; 0.49 g (74% yield). MS-APCI: M+1=582.5.

Analysis calculated for $C_{34}H_{39}N_5O_4 \cdot 0.3H_2O$: C, 69.56; H, 6.80; N, 11.93.

Found: C, 69.37; H, 6.64; N, 12.03.

EXAMPLE 3

Benzyl N-[(1S)-1-(1H-4-imidazolylmethyl)-2-((2-methyl-2-phenylpropyl)2-[(2-methyl-2-phenylpropyl)amino]-2-oxoethylamino)-2-oxoethyl]carbamate The title compound can be prepared according to Example 1 by substituting β,β-dimethylphenethylamine hydrochloride (Example 1, Step 6) for (S)-α-methylbenzylamine in Step 1. The title compound is obtained as a white foam; 0.60 g (68% yield). MS-APCI: M+1=610.5.

Analysis calculated for $C_{36}H_{43}N_5O_4 \cdot 0.75H_2O$: C, 69.37; H, 7.20; N, 11.24.

Found: C, 69.46; H, 7.01; N, 11.41.

EXAMPLE 4

Methyl 3-([(2S)-2-[(benzyloxy)carbonyl]amino-3-(1H-4-imidazolyl)propanoyl]-2-[(2-methyl-2-phenylpropyl)amino]-2-oxoethylamino)propanoate

Step 1: 3-(tert-Butoxycarbonylmethyl-amino)-propionic acid methyl ester

Triethylamine (7 mL, 50 mmol) was added to a solution of β-alanine methyl ester hydrochloride (5.25 g, 37.5 mmol) in methylene chloride (100 mL). The solution was cooled to 0° C. and t-butyl bromoacetate (4.88 g, 25 mmol) in methylene chloride (100 mL) was then added. The reaction mixture was warmed to room temperature and stirred overnight. The solvent was removed in vacuo and the residue was taken up in ethyl acetate. The ethyl acetate was washed with saturated $NaHCO_3$, brine, dried over $MgSO_4$, filtered and concentrated in vacuo; 0.80 g (14% yield).

Step 2: (S)3-{[2-Benzyloxycarbonylamino-3-(1-trityl-1H-imidazol-4-yl)-propionyl]-tert-butoxycarbonylmethyl-amino}-propionic acid methyl ester To a solution of the compound from Step 1 (0.434 g, 2 mmol) in methylene chloride (10 mL) was added Cbz-His (Trt)-OH (1.062 g, 2 mmol), triethylamine (0.8 mL, 5.7 mmol) and HBTU (0.758 g, 2 mmol) dissolved in acetonitrile (10 mL). The reaction mixture was stirred overnight at room temperature. The solution was concentrated, the residue taken up in ethyl acetate and washed three times with saturated $NaHCO_3$, brine, dried over $MgSO_4$, filtered and concentrated in vacuo. Chromatography was carried out on silica gel, using 30% hexanes in ethyl acetate as eluent, to give an oil; 1.38 g (94% yield). MS-APCI: M+1=732.

Step 3: (S)3-{[2-Benzyloxycarbonylamino-3-(1H-imidazol-4-yl)-propionyl]-carboxymethyl-amino}-propionic acid methyl ester The compound from Step 2 (1.38 g, 1.9 mmol) was treated with 95% aqueous trifluoroacetic acid for 1.5 hours. The solvent was reduced to a few milliliters, and pipetted into 200 mL of ether/hexanes. The product was allowed to precipitate overnight at −40° C. The solid was collected, rinsed and dried; 0.75 g (91% yield).

Step 4: Methyl 3-([(2S)-2-[(benzyloxy)carbonyl]amino-3-(1H-4-imidazolyl)propanoyl]-2-[(2-methyl-2-phenylpropyl)amino]-2-oxoethylamino)propanoate The compound from Step 3 (0.75 g, 1.74 mmol) was dissolved in 1:1 dimethylformamide:methylene chloride (5 mL each).β,β-dimethylphenethylamine hydrochloride (Example 1, Step 6) (0.325 g, 1.75 mmol) was added followed by diisopropylethylamine (1 mL, 5.7 mmol) and HBTU (0.760 g, 2 mmol) dissolved in dimethylformamide (10 mL). The reaction was stirred overnight at room temperature. The solution was concentrated, the residue taken up in ethyl acetate and washed three times with saturated $NaHCO_3$, brine, dried over $MgSO_4$, filtered and concentrated in vacuo. Chromatography was carried out on silica gel, using 5% methanol in methylene chloride as eluent, to give a white foam; 0.50 g (5 1 % yield). MS-APCI: M+1=564.4.

Analysis calculated for $C_{30}H_{36}N_5O_6 \cdot 2.61H_2O \cdot 1.37\ CH_2Cl_2$: C, 51.90; H, 6.10; N, 9.65.

Found: C, 51.87; H, 6.06; N, 9.72.

EXAMPLE 5

3-([(2S)-2-[(Benzyloxy)carbonyl]amino-3-(1H-4-imidazolyl)propanoyl]-2-[(2-methyl-2-phenylpropyl)amino]-2-oxoethylamino)propanoic acid

Step 1: 3-([(2S)-2-[(Benzyloxy)carbonyl]amino-3-(1H-4-imidazolyl)propanoyl]-2-[(2-methyl-2-phenylpropyl)amino]-2-oxoethylamino)propanoic acid The product from Example 4 (0.30 g, 0.53 mmol) was dissolved in tetrahydrofuran (10 mL), methanol (10 mL) and water (1 mL). Sodium hydroxide (42 mg, 1.05 mmol) was added and the reaction was stirred overnight at room temperature. The solution was concentrated in vacuo and the residue taken up in 0.1 M $NaPO_4$ buffer (100 mL). The pH was brought to 6 by the addition of 1N HCl. The product was extracted three times with ethyl acetate. The ethyl acetate was washed twice with brine, dried over $MgSO_4$, filtered and concentrated in vacuo. Purification was carried out via reversed-phase HPLC (0.1 % trifluoroacetic acid in acetonitrile and 0.1% aqueous trifluoroacetic acid as eluent; C-18 column) to give a white powder; 0.078 g (27% yield). MS-APCI: M+1=550.3.

Analysis calculated for $C_{29}H_{34}N_5O_6 \cdot 1.46CF_3COOH$, $1.62H_2O$: C,51.51; H,5.24; N, 9.41.

Found: C, 51.51; H, 5.27; N, 9.40.

EXAMPLE 6

[1-{(2-Amino-ethyl)-[(2-methyl-2-phenyl-propylcarbamoyl)-methyl]-carbamoyl}-2-(3H-imidazol-4-yl)-ethyl]-carbamic acid benzyl ester

Step 1: (2-tert-Butoxycarbonylamino-ethylamino)-acetic acid methyl ester

To a solution of (2-aminoethyl)carbamic acid tert-butyl ester (from Step 6 below) (4.2 g, 26.3 mmol) in methylene chloride (50 mL) was added triethylamine (4.4 mL, 31.4 mmol) and methyl bromoacetate (2.4 mL, 26.3 mmol). The reaction was stirred overnight at room temperature. A saturated aqueous solution of sodium chloride (100 mL) was then added, and the organic layer was separated dried over MgSO$_4$, filtered and concentrated. The residue was taken up in diethyl ether, and a saturated solution of HCl in diethyl ether was added to precipitate the product, which was filtered, and dried. It was recrystallized in ethanol/ethyl acetate, to give a white solid; 1.39 g (20% yield). MS-APCI: M+1=233.

Step 2: (S)[[2-Benzyloxycarbonylamino-3-(1-trityl-1H-imidazol-4-yl)-propionyl]-(2-tert-butoxycarbonylamino-ethyl)-amino]-acetic acid methyl ester The product from Step 1 (0.67 g, 2.5 mmol) was dissolved in methylene chloride (10 mL) and Cbz-His(Trt)-OH (1.46 g, 2.75 mmol) was then added, followed by diisopropylethylamine (1.3 mL, 7.5 mmol), HATU (1.05 g, 2.76 mmol), HOAt (0.374 g, 2.75 mmol), and dimethylformamide (10 mL). The reaction was stirred overnight at room temperature. The solution was concentrated, the residue taken up in ethyl acetate and washed three times with saturated NaHCO$_3$, brine, dried over MgSO$_4$, filtered and concentrated in vacuo to give a white solid; 1.8 g (97% yield). MS-APCI: M+1=747.

Step 3: (S)[[2-Benzyloxycarbonylamino-3-(1-trityl-1H-imidazol-4-yl)-propionyl]-(2-tert-butoxycarbonylamino-ethyl)-amino]-acetic acid The product from Step 2 (1.8 g, 2.4 mmol) was dissolved in tetrahydrofuran (10 mL), methanol (10 mL) and water (2 mL). Sodium hydroxide (0.192 g, 4.8 mmol) was added and the mixture stirred overnight at room temperature. The solution was concentrated in vacuo and the residue taken up in 0.1 M NaPO$_4$ buffer (100 mL). The pH was brought to 6 by the addition of 1N HCl. The product was extracted three times with ethyl acetate. The ethyl acetate was washed twice with brine, dried over MgSO$_4$, filtered and concentrated in vacuo to give a white powder; 1.3 g (74% yield). MS-APCI: M+1=732.

Step 4: (S)[1-{(2-tert-Butoxycarbonylamino-ethyl)-[(2-methyl-2-phenyl-propylcarbamoyl)-methyl]-carbamoyl}-2-(1-trityl-1H-imidazol-4-yl)-ethyl]-carbamic acid benzyl ester The compound from Step 3 (1.3 g, 1.8 mmol) was dissolved in methylene chloride (10 mL). β,β-dimethylphenethylamine hydrochloride (Example 1, Step 6) (0.370 g, 2 mmol) was added followed by diisopropylethylamine (1 mL, 5.7 mmol) and PyBOP (1.04 g, 2 mmol) dissolved in methylene chloride (10 mL). The reaction was stirred overnight at room temperature. The solution was concentrated, the residue taken up in ethyl acetate and washed three times with saturated NaHCO$_3$, brine, dried over MgSO$_4$, filtered and concentrated to give a white solid; 1.09 g (70% yield). MS-APCI: M+1=863.

Step 5: [1-{(2-Amino-ethyl)-[(2-methyl-2-phenyl-propylcarbamoyl)-methyl]-carbamoyl}-2-(3H-imidazol-4-yl)-ethyl]-carbamic acid benzyl ester The compound from Step 4 (1.09 g, 1.26 mmol) was treated with 95% aqueous trifluoroacetic acid (50 mL) for 1 hour at room temperature. The solvent was reduced to a few milliliters, and pipetted into 200 mL of ether/hexanes. The product was allowed to precipitate overnight at −40° C. The solid was collected, rinsed and dried. Purification was carried out via reversed-phase HPLC (0.1% trifluoroacetic acid in acetonitrile and 0.1% aqueous trifluoroacetic acid as eluent; C-18 column) to give a white powder; 0.30 g (45% yield). MS-APCI: M+1=521.2.

Analysis calculated for $C_{28}H_{35}N_6O_4 \cdot 2.07 CF_3COOH$, $1.08 H_2O$: C, 49.80; H, 5.10; N, 10.84.

Found: C, 49.83; H, 5.15; N, 10.82.

Step 6: (2-aminoethyl)carbamic acid tert-butyl ester

To a cooled solution of ethylenediamine (6.7 mL, 0.1 mol) in tetrahydrofuran (30 mL) was added di-t-butyl dicarbonate (7.27 g, 0.033 mol) dissolved in tetrahydrofuran (30 mL), over 30 minutes. After the addition was complete, the reaction mixture was stirred overnight at room temperature. The solution was concentrated and the residue taken up in ethyl acetate. The organic solution was washed with brine, dried over MgSO$_4$, filtered and concentrated to give a white paste; 4.2 g, (79% yield). MS-APCI: M+1=161. It was used without further purification.

EXAMPLE 7

Benzyl N-[(1S)-1-(1H-4-imidazolylmethyl)-2-([2-(methylamino)ethyl]-2-[(2-methyl-2-phenylpropyl)amino]-2-oxoethylamino)-2-oxoethyl]carbamate The title compound can be prepared according to Example 6, by substituting (2-amino-ethyl)-methyl-carbamic acid tert-butyl ester (Step 1, below) for (2-aminoethyl)-carbamic acid tert-butyl ester in Step 1. The title compound is obtained as a white foam; 0.40 g (32% yield). MS-APCI: M+1=535.5.

Analysis calculated for $C_{29}H_{38}N_6O_4 \cdot 0.26\ CH_2Cl_2$: C, 63.12; H, 6.97; N, 15.09.

Found: C, 63.06; H, 7.16; N, 15.17.

Step 1: (2-Amino-ethyl)-methyl-carbamic acid tert-butyl ester

To a cooled solution of methyl aminoacetonitrile hydrochloride (5.4 g, 50 mmol) in tetrahydrofuran:dimethylformamide (15 mL each) was added over 30 minutes, a solution of di-t-butyl dicarbonate (9.0 g, 50 mmol) and triethylamine (3.4 mL, 24 mmol) in tetrahydrofuran (30 mL). The reaction was stirred overnight at room temperature. The solution was concentrated and the residue taken up in ethyl acetate. The organic solution was washed with brine, dried over MgSO$_4$, filtered and concentrated to give a brownish oil; 8.38 g, (98% yield). MS-APCI: M+1=171. It was used without further purification.

The above product was reduced in the presence of Raney nickel, in ethanol/triethylamine. The catalyst was removed and washed with ethanol. The filtrate was concentrated to give the desired product as a brownish oil; 7.13 g (84% yield). MS-ACPI: M+1=175.

EXAMPLE 8

(2-(3H-Imidazol-4-yl)-1-{(2-methoxy-ethyl)-[(2-methyl-2-phenyl-propylcarbamoyl)-methyl]-carbamoyl}-ethyl)-carbamic acid benzyl ester The title compound can be prepared according to Example 6 by substituting 2-methoxyethylamine for (2-aminoethyl)-carbamic acid tert-butyl ester in Step 1. The title compound is obtained as a white foam; 0.33 g (24% yield). MS-APCI: M+1=536.2.

Analysis calculated for $C_{29}H_{37}N_5O_5 \cdot 0.22$ $CH_2Cl_2$: C, 63.31; H, 6.81; N, 12.63.

Found: C, 63.30; H, 6.69; N, 12.91.

EXAMPLE 9

Benzyl N-[2-((E)-2-butenyl-2-[(2-methyl-2-phenylpropyl)amino]-2-oxoethylamino)-1-(1H-4-imidazolylmethyl1)-2-oxoethyl]carbamate Step 1: Methyl 2-[(E)-2-butenylamino]acetate A suspension of (E)-2-buten-1-amine HCl (5.37 g, 49.9 mmol) (Chem. Ber. 117, 1250(1984) in acetonitrile (100 mL) was treated with methyl bromoacetate (4.72 mL, 49.9 mmol) and $Et_3N$ (14.0 mL, 99.8 mmol) and stirred at room temperature for I hour. The suspension was then heated at reflux overnight. Solution occurred at reflux temperature. After cooling, the precipitated $Et_3N \cdot HCl$ was filtered off and the solvent removed under reduced pressure leaving 5.0 g of the crude product. Chromatography on silica gel, eluting with $CHCl_3$/MeOH (98/2) gave 1.41 g (19.8% yield) of the pure product as an oil.

Step 2: Methyl 2-[2-[(benzyloxy)carbonyl]amino-3-(1-trityl-1H-5-imidazolyl)propanoyl][(E)-2-butenyl]aminoacetate A solution of methyl 2-[(E)-2-butenylamino]acetate (0.6 g, 4.2 mmol) in $CH_2Cl_2$ (50 mL) was cooled in ice and treated with 2.23 g (4.2 mmol) of Cbz-His(Trt)-OH (2.23 g, 4.2 mmol), diisopropylethylamine (2.2 mL, 12.6 mmol), and PyBOP (2.2 g, 4.2 mmol). After stirring at 0° for 15 minutes, the solution was allowed to stir at room temperature for 4 days. After removal of the solvent under reduced pressure, the residue was taken up in EtOAc, washed three times with $H_2O$, then with saturated NaCl. Drying over $MgSO_4$ and removal of the solvent under reduced pressure left 4.36 g of the crude product. Chromatography on silica gel, eluting with $CHCl_3$/MeOH (98/2) gave 2.23 g (81.1% yield) of the pure product as a white solid foam. MS, m/z 657 (M+H$^+$).

Step 3: 2-[2-[(Benzyloxy)carbonyl]amino-3-(1-trityl-1H-5-imidazolyl)propanoyl][(E)-2-butenyl]aminoacetic acid A solution of methyl 2-[2-[(benzyloxy)carbonyl]amino-3-(1-trityl-1H-5-imidazolyl)propanoyl][(E)-2-butenyl]aminoacetate (2.23 g, 3.4 mmol) in MeOH (20 mL)/dioxane (15 mL) was treated with 2 N NaOH (7.0 mL, 14.0 mmol) and stirred at room temperature for 0.5 hour. After adding 2 N HCl (7.0 mL, 14.0 mmol), the mixture was stripped to a solid. This was mixed with EtOAc/THF and filtered to remove NaCl. Removal of the solvent under reduced pressured left 2.06 g (94.5% yield) of the product as a white solid foam. MS, rn/z 643 (M+H$^+$).

Step 4: Benzyl N-2-((E)-2-butenyl-2-[(2-methyl-2-phenylpropyl)amino]-2-oxoethylamino)-2-oxo-1-[(1-trityl-1H-4-imidazolyl)methyl]ethylcarbamate A solution of 2-[2-[(benzyloxy)carbonyl]amino-3-(1-trityl-1H-5-imidazolyl)propanoyl][(E)-2-butenyl]aminoacetic acid (1.0 g, 1.6 mmol) in THF (20 mL) was treated with HOBt (0.22 g, 1.6 mmol) and DCC (0.33 g, 1.6 mmol). β,β-dimethylphenethylamine hydrochloride (Example 1, Step 6) (0.29 g, 1.6 mmol) was then added, followed by $Et_3N$ (0.22 mL, 1.6 mmol) and the mixture stirred at room temperature for 2 days. The mixture was diluted with EtOAc, filtered, and the filtrate washed with saturated $NaHCO_3$ and saturated NaCl. Drying over $MgSO_4$ and removal of the solvent under reduced pressure gave 1.19 g (99.2% yield) of the product as a white foam. MS, m/z 774 (M+H$^+$).

Step 5: Benzyl N-[2-((E)-2-butenyl-2-[(2-methyl-2-phenylpropyl)amino]-2-oxoethylamino)-1-(1H-4-imidazolylmethyl)-2-oxoethyl]carbamate A solution of benzyl N-2-((E)-2-butenyl-2-[(2-methyl-2-phenylpropyl)amino]-2-oxoethylamino)-2-oxo-1-[(1-trityl-1H-4-imidazolyl)methyl]ethylcarbamate (1.19 g, 1.6 mmol) in 80% aqueous HOAc (100 mL) was heated at 87° C. for 0.5 hours. The solvent was removed under reduced pressure and the residue taken up in EtOAc and washed twice with saturated $NaHCO_3$, then saturated NaCl. Drying over $MgSO_4$ and removal of the solvent under pressure gave the crude product. Chromatography on silica gel, eluting with $CHCl_3$/MeOH (95/5) gave the product which was dissolved in $CH_2Cl_2$ and the solvent removed under reduced pressure to give 0.64 g (74.4% yield) of the product as a solid foam. MS, m/z 532 (M+H$^+$).

Analysis calculated for $C_{30}H_{37}N_5O_4 \cdot 0.1$ $CH_2Cl_2$: C, 66.93; H, 6.94; N, 12.97.

Found: C, 66.68; H, 7.01; N, 12.96.

EXAMPLE 10

[1-{(4-Benzyloxy-benzyl)-[(2-methyl-2-phenyl-propylcarbamoyl)-methyl]-carbamoyl}-2-(1H-imidazol-4-yl)-ethyl]-carbamic acid 1-phenyl-ethyl ester The title compound can be prepared according to Example 9 by substituting 2-(1-phenyl-ethoxy-carbonylamino)-3-(1-trityl-1H-imidazol-4-yl)-propionic acid (Steps 1 and 2, below) for Cbz-His(Trt)-OH in Example 9, Step 2. The title compound is obtained as a white foam; 0.264 g (46% yield). MS-APCI: M+1=688.5.

Analysis calculated for $C_{41}H_{45}N_5O_5 \cdot 0.13$ $CH_2Cl_2$: C, 70.65; H, 6.53; N, 10.02.

Found: C, 70.65; H, 6.47; N, 10.08.

Step 1: 2-(1-Phenyl-ethoxycarbonylamino)-3-(1-trityl-1H-imidazol-4-yl)-prionic acid methyl ester A solution of α-methylphenethanol (0.55 mL, 4.6 mmol), 4-nitrophenylchloroformate (0.92 g, 4.6 mmol) and triethylamine (0.64 mL, 4.6 mmol) in methylene chloride (20 mL) was cooled to 0° C. After 15 minutes, His(Trt)-OCH$_3$ ((2 g, 4.2 mmol) and triethylamine (1.28 mL, 9.1 mmol) in methylene chloride (10 mL) were added. The reaction was stirred overnight at room temperature. The solution was washed twice with water, saturated $NaHCO_3$, brine, dried over $MgSO_4$, filtered and concentrated. Chromatography was carried out on silica gel, using 70%–80% ethyl acetate in hexanes as eluent, to give a white foam; 1.26 g (54% yield). MS-APCI: M+1=560.3.

Step 2: 2-(1-Phenyl-ethoxycarbonylamino)-3-(1-trityl-1H-imidazol-4-1 )-propionic acid The compound from Step 1 (1.06 g, 1.9 mmol) was dissolved in methanol (10 mL) and tetrahydrofaran (10 mL), and 1N NaOH (5.7 mL, 5.7 mmol) was then added and the reaction stirred at room temperature for 2 hours. The solution was concentrated. HCl (1N) (5.7 mL, 5.7 mmol) was added and the product extracted with ethyl acetate. The organic solution was washed with brine, dried over MgSO$_4$, filtered and concentrated to give a white foam; 1.0 g (96% yield).

EXAMPLE 11

Benzyl N-(1S)-1-(1H-4-imidazolylmethyl)-2-[2-[(2-methyl-2-phenylpropyl)amino]-2-oxoethyl(2-morpholinoethyl)amino]-2-oxoethylcarbamate The title compound can be prepared according to Example 6 by substituting 2-morpholinoethylamine for (2-aminoethyl)-carbamic acid tert-butyl ester in Step 1. The title compound is obtained as a white foam; 0.055 g (15% yield). MS-APCI: M+1=591.2.

Analysis calculated for $C_{32}H_{42}N_6O_5 \cdot 0.92\ H_2O$, 2.34 CF$_3$COOH: C, 50.40; H, 5.33; N, 9.61.

Found: C, 50.37; H, 5.28; N, 9.60.

EXAMPLE 12

3-{[2-Benzyloxycarbonylamino-3-(3H-imidazol-4-yl)-propionyl]-[(2-methyl-2-phenyl-prolylcarbamoyl)-methyl]-amino}-propionic acid isopropyl ester The product from Example 5 (0.22 g, 0.4 mmol) was dissolved in 20% isopropanol in methylene chloride (10 mL). Diisopropylethylamine (0.42 mL, 2.4 mmol) was added and the reaction was cooled to 0° C. PyBOP (0.42 g, 0.8 mmol) in methylene chloride (5 mL) was then added. The reaction was allowed to warm to room temperature and stirred overnight. The solution was concentrated, the residue taken up in ethyl acetate and washed three times with saturated NaHCO$_3$, brine, dried over MgSO$_4$, filtered and concentrated in vacuo. Purification was carried out via reversed-phase HPLC (0.1% trifluoroacetic acid in acetonitrile and 0.1% aqueous trifluoroacetic acid as eluent; C-18 column) to give a white powder; 0.012 g (5% yield). MS-APCI: M+1=592.2.

Analysis calculated for $C_{32}H_{41}N_5O_6 \cdot 1.32$ CF$_3$COOH, 1.03H$_2$O: C, 54.69; H, 5.88; N, 9.21.

Found: C, 54.49; H, 5.47; N, 9.59.

EXAMPLE 13

[1-{(2-Dimethylcarbamoyl-ethyl )-[(2-methyl-2-phenyl-propylcarbamoyl)-methyl]-carbamoyl}-2-(3H-imidazol-4-yl)ethyl]-carbamic acid benzyl ester The product from Example 5 (0.48 g, 0.87 mmol) was dissolved in methylene chloride (5 mL) and dimethylformamide (5 m). Diisopropylethylamine (0.9 mL, 5.2 mmol) and dimethylamine hydrochloride (0.144 g, 1.76 mmol) were added and the reaction was cooled to 0° C. PyBOP (0.91 g, 1.75 mmol) in methylene chloride (5 mL) was then added. The reaction was allowed to warm to room temperature and stirred overnight. The solution was concentrated, the residue taken up in ethyl acetate and washed three times with saturated NaHCO$_3$, brine, dried over MgSO$_4$, filtered and concentrated in vacuo. Purification was carried out via reversed-phase HPLC (0.1% trifluoroacetic acid in acetonitrile and 0.1% aqueous trifluoroacetic acid as eluent; C-18 column) to give a white powder; 0.115 g (23% yield). MS-APCI: M+1=577.3.

Analysis calculated for $C_{31}H_{40}N_6O_5 \cdot 1.50$ CF$_3$COOH, 0.90H$_2$O: C, 53.46; H, 5.71; N, 11.0.

Found: C, 53.40; H, 5.60; N, 11.40.

EXAMPLE 14

{2-(3H-Imidazol-4-yl)-1-[[(2-methyl-2-phenyl-propylcarbamoyl)-methyl]-(2-methylsulfanyl-ethyl)-carbamoyl]-ethyl}-carbamic acid benzyl ester The title compound can be prepared according to Example 4, substituting 2-thiol-ethylamine for β-alanine methyl ester hydrochloride in Step 1. The title compound is obtained as a white foam; 0.12 g (10% yield). MS-APCI: M+1=552.3.

Analysis calculated for $C_{29}H_{37}N_5O_4S_1 \cdot 1.04$ CF$_3$COOH, 0.53H$_2$O: C, 54.91; H, 5.80; N, 10.30.

Found: C, 54.90; H, 5.80; N, 10.60.

| | |
|---|---|
| HPLC | High pressure liquid chromatography |
| CI-MS | Chemical Ionization Mass Spectrometry |
| mp | Melting point |
| rt | Room temperature |
| THF | Tetrahydrofuran |
| APCI-MS | Atmospheric pressure chemical ionization mass spectrometry |
| dec | Decomposes |
| AcCN, CH$_3$CN, or MeCN | Acetonitrile |
| HOAc | Acetic acid |
| CHCl$_3$ | Chloroform |
| DCM | Dichloromethane or methylene chloride |
| DMF | N,N'-Dimethylformamide |
| EtOAc | Ethyl acetate |
| EtOH | Ethanol |
| Et$_2$O | Diethyl ether |
| HCl | Hydrochloric acid |
| H$_2$O$_2$ | Hydrogen peroxide |
| H$_2$SO$_4$ | Sulfuric acid |
| KOH | Potassium hydroxide |
| MeOH | Methanol |
| NaH | Sodium hydride |
| NaOH | Sodium hydroxide |
| NaHCO$_3$ | Sodium bicarbonate |
| iPrOH | iso-Propanol |
| TFA | Trifluoroacetic acid |
| Boc | tertiary Butyloxycarbonyl |
| Ts | Tosylate |
| Ph$_3$P | Triphenylphosphine |
| HATU | O-(7-azabenzotriazol-1-yl)-N,N,N',N'-tetramethyluronium hexafluorophosphate |
| HBTU | O-benzotriazol-1-yl-N,N,N',N'-tetramethyl-uronium hexafluorophosphate |
| PyBOP | Benzotriazole-1-yl-oxy-tris-pyrrolidino-phosphonium hexafluorophosphate |
| Et$_3$N, TEA | Triethylamine |
| DIEA | Diisopropylethylamine |
| Trt | Trityl |
| HOAt | 1-Hydroxy-7-azabenzotriazole |

When indicated, analytical HPLC was performed on Vydac C18 peptide/protein columns eluting with gradients of water/acetonitrile containing 0.1% TFA. Flash chromatography was performed using Merck or ICN silica gel, 60A, 230–400 mesh. THF was distilled from Na/benzophenone and all other solvents were reagent grade and dried over 4A molecular sieves unless otherwise indicated.

The data in the table below shows the farnesyl protein transferase inhibitory activity of compounds of the present invention.

| Example Number | IC$_{50}$ ($\mu$M) Hepes | IC$_{50}$ ($\mu$M) Hepes/5 mM KPO$_4^{-2}$ | Gel Shift ($\mu$M) MED |
|---|---|---|---|
| 1 | 0.57 | 0.001 | 0.01 |
| 2 | 8.3 | 0.065 | 1 |
| 3 | 0.098 | 0.001 | 0.01 |
| 4 | 5.0 | 0.018 | 0.1 |
| 5 | 2.3 | <0.001 | 1 |
| 6 | 36 | 0.072 | >1 |
| 7 | >30 | 0.92 | |
| 8 | 4.8 | 0.019 | 0.2 |
| 9 | 1.4 | 0.011 | 0.01 |
| 10 | 0.25 | 0.004 | 0.01 |
| 11 | 2.1 | 0.016 | 0.2 |
| 12 | 2.2 | 0.034 | |
| 13 | 4.0 | 0.007 | |
| 14 | 1.2 | 0.006 | 0.05 |

In general, the IC$_{50}$ represents the average of two tests.

What is claimed is:

1. A compound having the Formula I $$A-\underset{\underset{R^3}{|}}{\overset{O}{C}}-\underset{}{N}-\underset{\underset{R^4}{|}}{\overset{R^1}{C}}-\underset{}{\overset{O}{C}}-N-\underset{}{\overset{R^1}{CH}}-\underset{}{\overset{O}{C}}-\underset{\underset{R^5}{}}{N}\overset{R^1}{}\quad I$$

wherein

A is $$-N\overset{R^a}{\underset{R^b}{}},\quad -OR^a,\quad \text{or}\quad -O\underset{\underset{R^b}{|}}{\overset{R^a}{C}H};$$

each $R^1$ and $R^b$ are independently hydrogen or $C_1$–$C_6$ alkyl;

each $R^a$ is independently $C_1$–$C_6$ alkyl, —(CH$_2$)$_m$-aryl, —(CH$_2$)$_m$-substituted aryl, —(CH$_2$)$_m$-substituted heteroaryl, or —(CH$_2$)$_m$-heteroaryl;

each m is independently 0 to 3;

each n is independently 1 to 4;

$R^3$ is imidazolyl-(CH$_2$)$_n$– with $R^b$, or $R^b$–imidazolyl-(CH$_2$)$_n$–;

$R^4$ is

—CH(phenyl)(C$_1$–C$_6$alkyl), —(CH$_2$)$_n$—NH$_2$, —(CH$_2$)$_n$—NH(C$_1$–C$_6$alkyl), —(CH$_2$)$_n$—N(C$_1$–C$_6$alkyl)$_2$, —(CH$_2$)—C(phenyl)(C$_1$–C$_6$alkyl)$_2$, —(CH$_2$)$_n$—OC$_1$–C$_6$alkyl, —(CH$_2$)$_n$—OH, —(CH$_2$)$_n$—COH, —(CH$_2$)$_n$—COC$_1$–C$_6$alkyl, C$_2$–C$_6$alkenyl, (CH$_2$)$_n$-morpholino, —(CH$_2$)$_n$-piperidine-NH, —(CH$_2$)$_n$—CN, —(CH$_2$)$_n$—C(O)NR$^b$R$^b$, —(CH$_2$)$_n$—SR$^b$, —(CH$_2$)$_n$—S(O)—R$^b$, —(CH$_2$)$_n$—SO$_2$R$^b$, —(CH$_2$)$_n$-piperazine-N-R$^b$ or —(CH$_2$)$_n$-piperidine-N-C$_1$–C$_6$alkyl;

$R^5$ is $$-\underset{\underset{R^1}{|}}{\overset{R^1}{C}}_n\text{-aryl},\quad \text{or}\quad -\underset{\underset{R^1}{|}}{\overset{R^1}{C}}_n\text{-substituted aryl};$$

and the pharmaceutically acceptable salts.

2. A compound in accordance with claim 1 wherein each $R^1$ is hydrogen.

3. A compound in accordance with claim 1 wherein A is —OCH$_2$-phenyl.

4. A compound in accordance with claim 1 wherein $R^5$ is

—CH$_2$—C(CH$_3$)$_2$—phenyl.

5. A compound of claim 1 wherein A is —OCH$_2$-phenyl; each $R^1$ is hydrogen; and $R^5$ is —CH$_2$—C(CH$_3$)$_2$—phenyl.

6. A compound having the Formula I, $$A-\underset{\underset{R^3}{|}}{\overset{O}{C}}-\underset{}{N}-\underset{\underset{R^4}{|}}{\overset{R^1}{C}}-\underset{}{\overset{O}{C}}-N-\underset{}{\overset{R^1}{CH}}-\underset{}{\overset{O}{C}}-\underset{\underset{R^5}{}}{N}\overset{R^1}{}\quad I$$

wherein

A is —OCH₂-phenyl, or

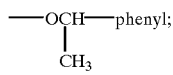

each R¹ is hydrogen;
R³ is

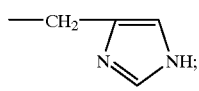

R⁴ is

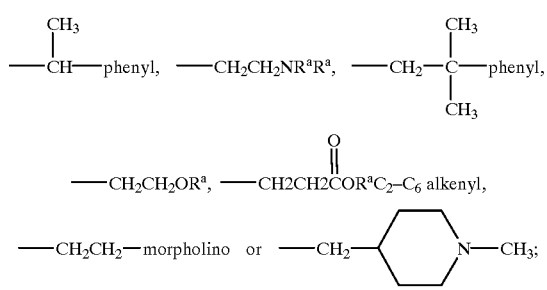

each R$^a$ is independently hydrogen or C₁–C₆ alkyl;
R⁵ is

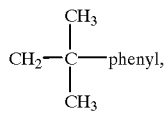

and the pharmaceutically acceptable salts.

7. A pharmaceutical composition comprising a compound of claim 1.

8. A pharmaceutical composition comprising a compound of claim 6.

9. A method of treating cancer, the method comprising administering to a patient having cancer a therapeutically effective amount of a compound of claim 1.

10. A method of treating cancer, the method comprising administering to a patient having cancer a therapeutically effective amount of a compound of claim 6.

11. A method of treating atherosclerosis, the method comprising administering to a patient having atherosclerosis a therapeutically effective amount of a compound of claim 1.

12. A method of treating atherosclerosis, the method comprising administering to a patient having atherosclerosis a therapeutically effective amount of a compound of claim 6.

13. A method of treating or preventing restenosis, the method comprising administering to a patient having restenosis or at risk of developing restenosis, a therapeutically effective amount of a compound of claim 1.

14. A method of treating or preventing restenosis, the method comprising administering to a patient having restenosis or at risk of developing restenosis, a therapeutically effective amount of a compound of claim 6.

15. The compound:

Benzyl N-((1S)-1-(1H-4-imidazolylmethyl)-2-2-[(2-methyl-2-phenylpropyl)amino]-2-oxoethyl[(1S)-1-phenylethyl]amino-2-oxoethyl)carbamate;

Benzyl N-((1S)-1-(1H-4-imidazolylmethyl)-2-2-[(2-methyl-2-phenylpropyl)amino]-2-oxoethyl[(1R)-1-phenylethyl]amino-2-oxoethyl)carbamate;

Benzyl N-[(1S)-1-(1H-4-imidazolylmethyl)-2-((2-methyl-2-phenylpropyl)2-[(2-methyl-2-phenylpropyl)amino]-2-oxoethylamino)-2-oxoethyl]carbamate;

Methyl 3-([[(2S)-2-[(benzyloxy)carbonyl]amino-3-(1H-4-imidazolyl)propanoyl]-2-[(2-methyl-2-phenylpropyl)amino]-2-oxoethylamino)propanoate;

3-([[(2S)-2-[(Benzyloxy)carbonyl]amino-3-(1H-4-imidazolyl)propanoyl]-2-[(2-methyl-2-phenylpropyl)amino]-2-oxoethylamino)propanoic acid;

[1-{(2-Amino-ethyl)-[(2-methyl-2-phenyl-propylcarbamoyl)-methyl]-carbamoyl}-2-(3H-imidazol-4-yl)-ethyl]-carbamic acid benzyl ester;

Benzyl N-[(1S)-1-(1H-4-imidazolylmethyl)-2-([2-(methylamino)ethyl]-2-[(2-methyl-2-phenylpropyl)amino]-2-oxoethylamino)-2-oxoethyl]carbamate;

(2-(3H-Imidazol-4-yl)-1-{(2-methoxy-ethyl)-[(2-methyl-2-phenyl-propylcarbamoyl)-methyl]-carbamoyl}-ethyl)-carbamic acid benzyl ester;

Benzyl N-[2-((E)-2-butenyl-2-[(2-methyl-2-phenylpropyl)amino]-2-oxoethylamino)-1-(1H-4-imidazolylmethyl)-2-oxoethyl]carbamate;

[1-{(4-Benzyloxy-benzyl)-[(2-methyl-2-phenyl-propylcarbamoyl)-methyl]-carbamoyl }-2-(1H-imidazol-4-yl)-ethyl]-carbamic acid 1-phenylethyl ester;

Benzyl N-(1S)-1-(1H-4-imidazolylmethyl)-2-[2-[(2-methyl-2-phenylpropyl)amino]-2-oxoethyl(2-morpholinoethyl)amino]-2-oxoethylcarbamate;

3-{[2-Benzyloxycarbonylamino-3-(3H-imidazol-4-yl)-propionyl]-[(2-methyl-2-phenyl-propylcarbamoyl)-methyl]-amino}-propionic acid isopropyl ester;

[1-{(2-Dimethylcarbarnoyl-ethyl)-[(2-methyl-2-phenyl-propylcarbamoyl)-methyl]-carbamoyl}-2-(3H-imidazol-4-yl)ethyl]-carbamic acid benzyl ester;

{2-(3H-Imidazol-4-yl)-1-[[(2-methyl-2-phenyl-propylcarbamoyl)-methyl]-(2-methylsulfanyl-ethyl)-carbamoyl]-ethyl}-carbamic acid benzyl ester;

Benzyl N-[(1S)-2-((2-hydroxyethyl)2-[(2-methyl-2-phenylpropyl)amino]-2-oxoethylamino)-1-(1H-4-imidazolylmethyl)-2-oxoethyl]carbamate; and Benzyl N-((1S)-1-(1H-4-imidazolylmethyl)-2-2-[(2-methyl-2-phenylpropyl)amino]-2-oxoethyl[(1-methyl-4-piperidyl)methyl]amino-2-oxoethyl)carbamate.

16. A compound having the Formula I

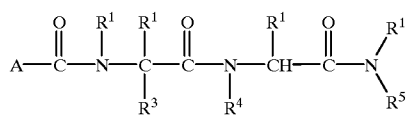

wherein A is
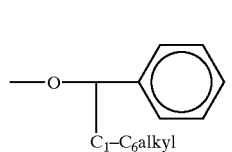 or 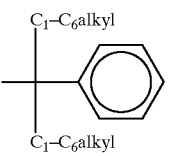;
each $R^1$ and $R^b$ are independently hydrogen or $C_1$–$C_6$ alkyl;
each $R^a$ is independently $C_1$–$C_6$ alkyl, —$(CH_2)_m$-aryl, —$(CH_2)_m$-substituted aryl, —$(CH_2)_m$-substituted heteroaryl, or —$(CH_2)_m$-heteroaryl;
each m is independently 0 to 3;
each n is independently 1 to 4;
$R^3$ is
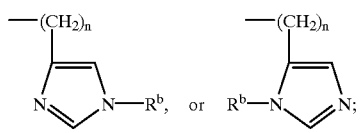
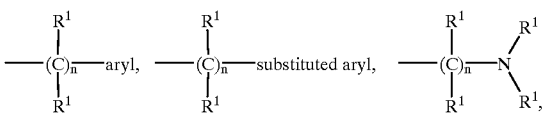
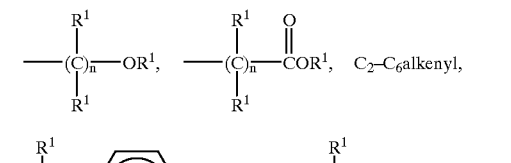
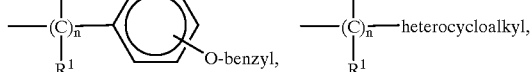
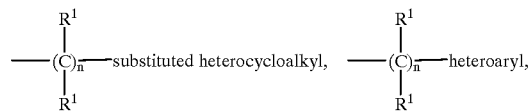
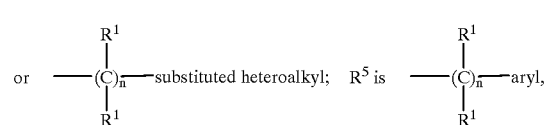
or 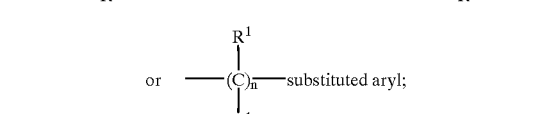
and the pharmaceutically acceptable salts.
* * * * *